(12) United States Patent  (10) Patent No.: US 8,666,492 B2
Muller et al.  (45) Date of Patent: *Mar. 4, 2014

(54) SAFETY SYSTEM FOR ELECTROSTIMULATION DEVICE

(71) Applicant: Complex Medical S.A., Ecublens (CH)

(72) Inventors: Pierre-Yves Muller, Collonge-Bellerive (CH); Klaus Schonenberger, Ecublens (CH)

(73) Assignee: Compex Medical S.A., Ecublens (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/710,842

(22) Filed: Dec. 11, 2012

(65) Prior Publication Data

US 2013/0172971 A1  Jul. 4, 2013

Related U.S. Application Data

(63) Continuation of application No. 10/585,796, filed as application No. PCT/IB2005/050048 on Jan. 5, 2005, now Pat. No. 8,335,566.

(30) Foreign Application Priority Data

Jan. 12, 2004  (CH) ........................................ 0040/04

(51) Int. Cl.
*A61N 1/08*  (2006.01)

(52) U.S. Cl.
USPC .................................... 607/36; 607/2; 607/63

(58) Field of Classification Search
USPC ............. 607/2, 4, 5, 9, 10, 33, 34, 36–38, 63, 607/115; 439/794, 796, 836, 837, 909
See application file for complete search history.

(56) References Cited

U.S. PATENT DOCUMENTS

| | | |
|---|---|---|
| 3,902,502 A | 9/1975 | Liss et al. |
| 3,942,535 A | 3/1976 | Schulman |
| 4,431,001 A | 2/1984 | Hakansson et al. |
| 4,759,368 A | 7/1988 | Spanton et al. |
| 4,770,328 A | 9/1988 | Dickhudt et al. |
| 5,314,451 A | 5/1994 | Mulier |
| 5,507,662 A | 4/1996 | Nyman |
| 5,573,551 A | 11/1996 | Lin et al. |
| 5,637,417 A | 6/1997 | Engmark et al. |
| 5,707,399 A | 1/1998 | Killander et al. |
| 5,758,414 A | 6/1998 | Ehrenfels et al. |
| 5,766,042 A | 6/1998 | Ries et al. |
| 5,807,144 A | 9/1998 | Sivard |
| 5,885,109 A | 3/1999 | Lee et al. |
| 6,070,103 A | 5/2000 | Ogden |
| 7,359,751 B1 | 4/2008 | Erickson et al. |
| 8,068,914 B1 | 11/2011 | Walsh et al. |
| 8,335,566 B2 | 12/2012 | Muller et al. |
| 2002/0116035 A1 | 8/2002 | Kiehn |

FOREIGN PATENT DOCUMENTS

FR  1503915  12/1967
WO  WO 2005/025012  3/2005

*Primary Examiner* — Allen Porter, Jr.
(74) *Attorney, Agent, or Firm* — Knobbe Martens Olson & Bear LLP

(57) ABSTRACT

A housing for an electrostimulation device comprising a charger plug and a stimulation plug, designed to receive respectively a connector linked to a charger and a connector linked to a stimulation electrode, characterized in that it comprises a mobile locking element designed to alternately lock the charger plug or the stimulation plug.

19 Claims, 8 Drawing Sheets

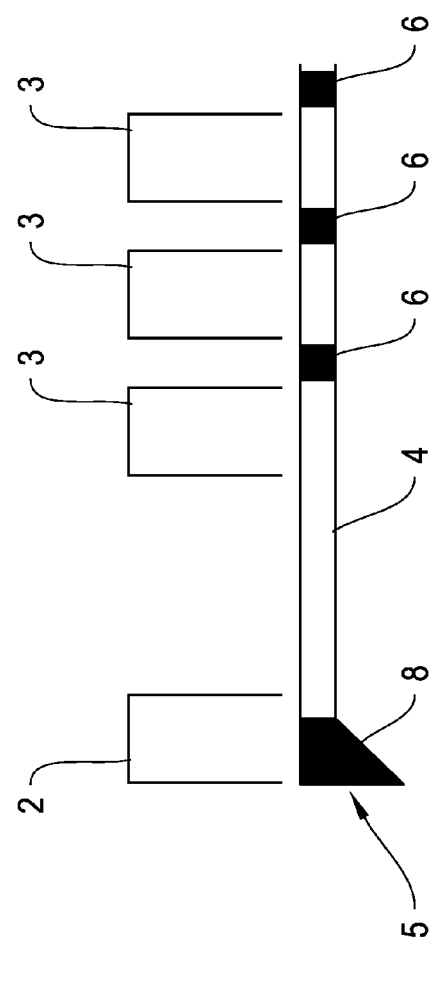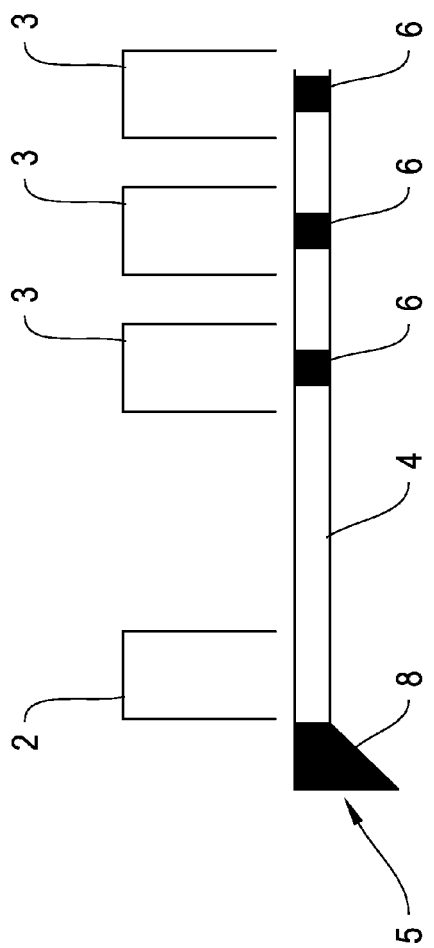

SAFETY SYSTEM FOR ELECTROSTIMULATION DEVICE

RELATED APPLICATION

This application claims the benefit of U.S. patent application Ser. No. 10/585,796, filed Jul. 23, 2008, and issued Dec. 18, 2012, as U.S. Pat. No. 8,335,566, which claims priority to PCT Application No. PCT/IB2005/050048 filed Jan. 5, 2005, and Swiss Patent Application No. 0040/04 filed Jan. 12, 2004, each of which is hereby incorporated by reference herein in its entirety.

BACKGROUND OF THE INVENTION

The present invention relates to the field of electrostimulation devices, in particular muscular electrostimulation devices.

More specifically, it relates to those electrostimulation devices that comprise a housing provided with at least one charger plug and one stimulation plug.

DESCRIPTION OF THE PRIOR ART

A number of styles of housings for electrostimulation devices are presented on the web site of the applicant (www.compex.info).

Normally, a housing for an electrostimulation device comprises a charger plug and a number of stimulation plugs designed to respectively receive a connector linked to an external charger and a number of connectors linked to stimulation electrodes.

The housing comprises an accumulator battery that is chargeable by direct current via the charger plug.

The electrostimulation is produced by means of electrodes applied to the skin of the user.

The stimulation current is limited to a few tens of milliamps (normally 120 mA maximum for a pulsed current).

A major risk is run by the user when the housing is linked both to the mains through the charger and to the user through the electrodes. In this configuration, if a fault were to occur in the external charger (insulation fault, component fault, etc.), the user could be directly linked to the mains voltage, which represents a mortal hazard. In practice, a link with the mains can provoke a cardiac fibrillation, a fainting fit, burns, pains, etc.

The housing disclosed in U.S. Pat. No. 4,421,001 offers a solution to this problem. It comprises a single plug that can operate alternately as a charger plug or a stimulation plug.

This solution does, however, present a number of drawbacks: it is not suited to housings that include a number of stimulation plugs and, furthermore, producing the dual-function plug is relatively complicated.

SUMMARY OF THE INVENTION

One objective of the invention is to increase the safety of the electrostimulation devices.

Another objective is to also offer a high level of safety for housings that include a number of stimulation plugs.

These objectives are achieved with a housing for an electrostimulation device that comprises a charger plug and a stimulation plug, designed to receive respectively a connector linked to a charger and a connector linked to stimulation electrodes. The housing according to the invention is characterized in that it also comprises a mobile locking element designed to alternately lock the charger plug or the stimulation plug.

The presence of the mobile locking element makes either the charger plug or the stimulation plug(s) available. The simultaneous availability of both types of plug is then impossible.

Particularly advantageous embodiments include a housing for an electrostimulation device that has a charger plug and a stimulation plug. The housing includes a mobile locking element that is designed to alternately lock the charger plug or stimulation plug. In another implementation, the mobile locking element presents an inclined surface inside the charger plug. Insertion of a connector into the charger plug exerts a force to displace the mobile locking element to lock the stimulation plug. In another implementation, the mobile locking element presents an inclined surface inside the stimulation plug. Insertion of a connector into the charger plug exerts a force to displace the mobile locking element to lock the charger plug. In another implementation, the charger plug and the stimulation plug are located on two opposite sides of the housing. The mobile locking element follows a curvilinear path. In another implementation the mobile locking element may include a thrust element which be activated by a user to release a plug.

Moving the mobile element from one position to the other can be done either manually, for example using a thrust element that the user moves, or as a consequence of inserting a connector into the plug that is blocked. In the latter case, the locking element comprises an inclined surface that is made apparent in the plug. When the connector is inserted into the plug, a force is exerted on the inclined surface, which causes the locking element to be displaced.

The invention will be better understood from reading the detailed description that follows and examining the appended drawings which represent, by way of nonlimiting example, an embodiment of the invention.

BRIEF DESCRIPTION OF THE DRAWINGS

FIG. 3 diagrammatically presents a locking principle according to the invention with stimulation plugs available.

FIG. 4 presents the object of FIG. 3 with a charger plug available.

DETAILED DESCRIPTION OF THE PREFERRED EMBODIMENTS

Figure 1:
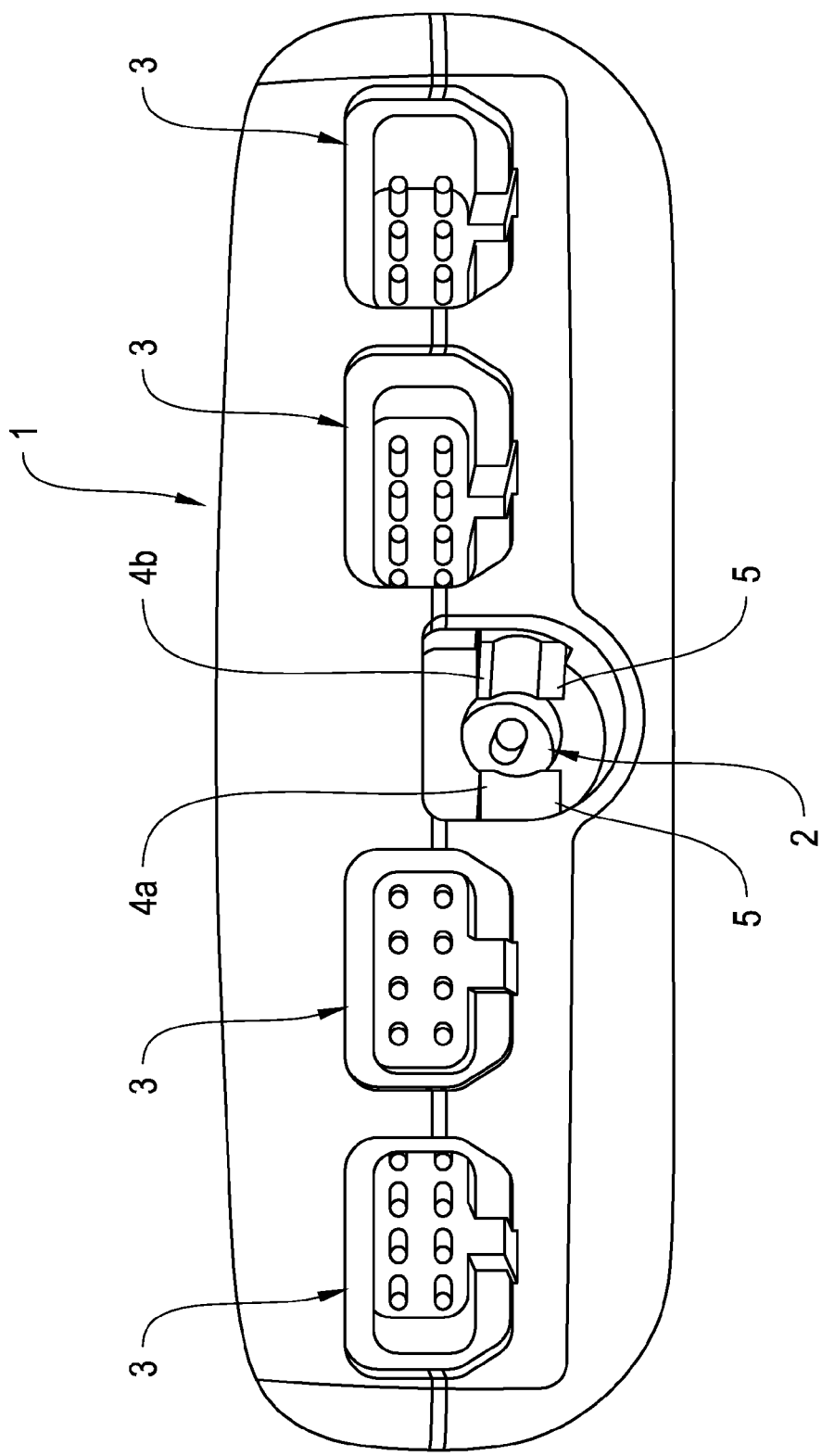
FIG. 1 presents a first embodiment of the invention with stimulation plugs available.

In the various FIGS. 1-11, illustrated are a housing 1, a charger plug 2, a stimulation plug 3, a mobile locking element 4, a locking element of the charger plug 5, a locking element of the stimulation plug 6, a thrust element 7, and an inclined surface 8.

Figure 2:
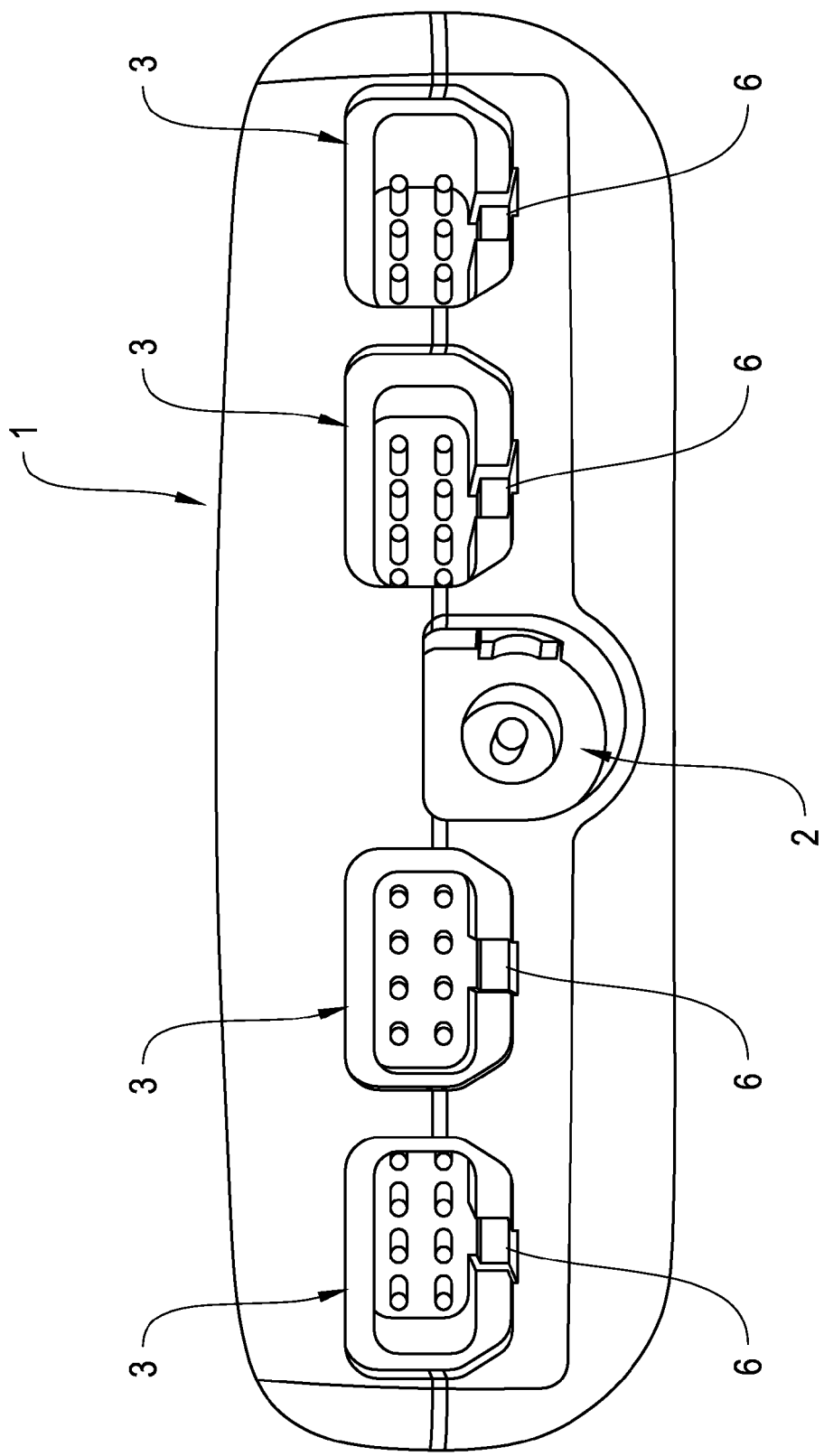
FIG. 2 presents the housing of FIG. 1 with a charger plug available.

The housing 1 represented in FIGS. 1 and 2 comprises a charger plug 2 and four stimulation plugs (each indicated by reference numeral 3).

FIGS. 3 and 4 diagrammatically represent in particular the design illustrated in FIGS. 1 and 2. The housing 1 comprises two mobile locking elements 4a and 4b in strip form, which can be displaced in a direction parallel to the line passing through the plugs 2, 3. Each of strips 4a and 4b comprises a series of teeth 6 designed to lock the stimulation plugs 3. The end of each strip 4a and 4b which culminates in the charger plug 2 comprises an inclined surface 8. When the charger connector is inserted into the corresponding plug 2, a force is exerted on the inclined surface 8, which drives the strips towards the stimulation plugs 3, simultaneously locking their access.

Preferably, springs (not shown) are associated with the locking strips 4a and 4b. They are located so as to return the locking strips 4a and 4b when all the connectors are removed from the housing 1.

The locking elements 6 can take the form of teeth, as indicated previously. Alternatively, the locking strip 4 can include orifices (not shown) through which the plugs can pass. In this case, the locking elements are formed by the strip elements that are located between the orifices.

Figure 5:
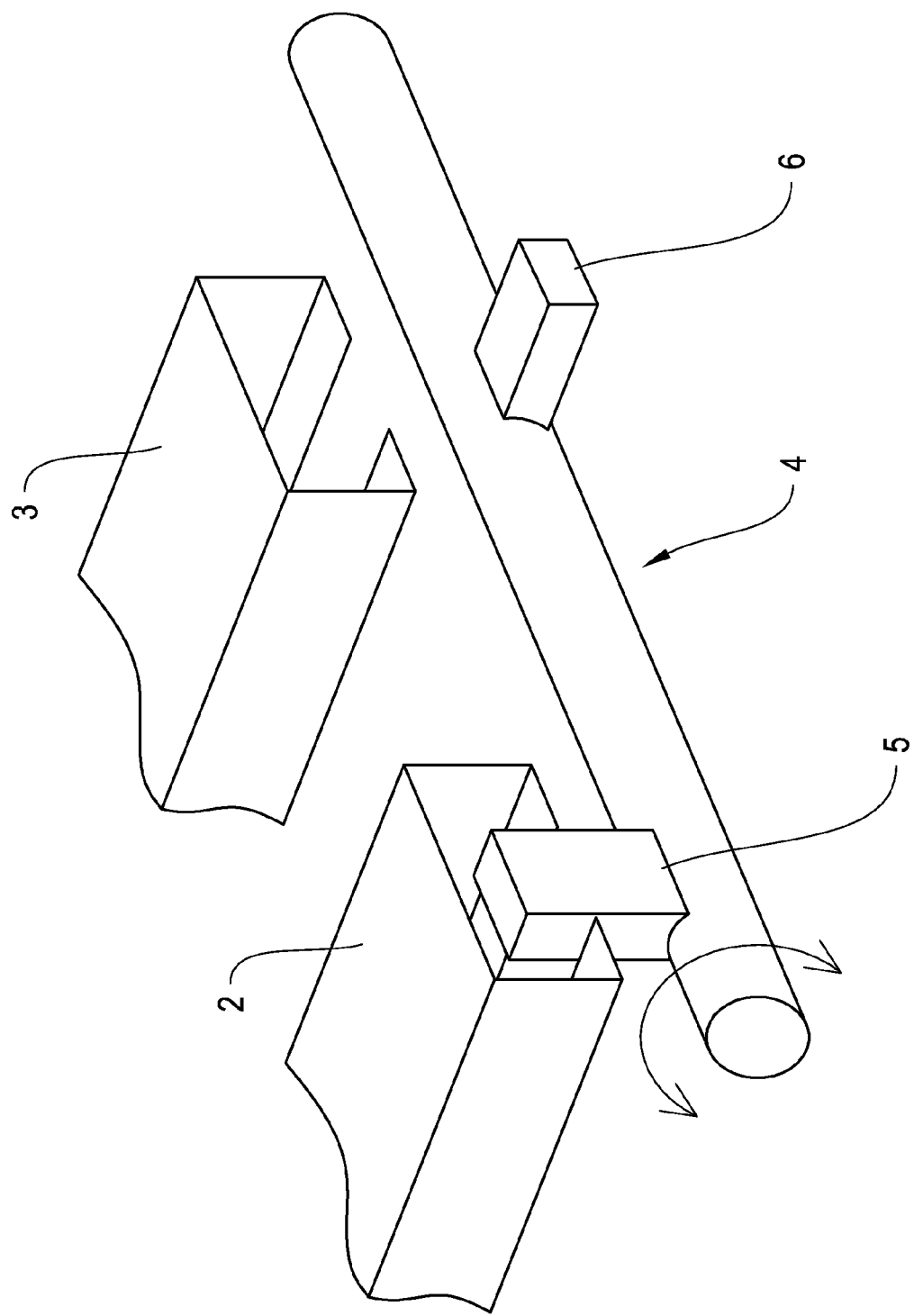
FIG. 5 presents a second embodiment of the invention.

The embodiment diagrammatically illustrated in FIG. 5 comprises a locking rod 4 which pivots about its main axis. The locking elements 6 are angularly separated by 90° so that the charger 2 and stimulation plugs 3 are alternately locked.

Figure 6:
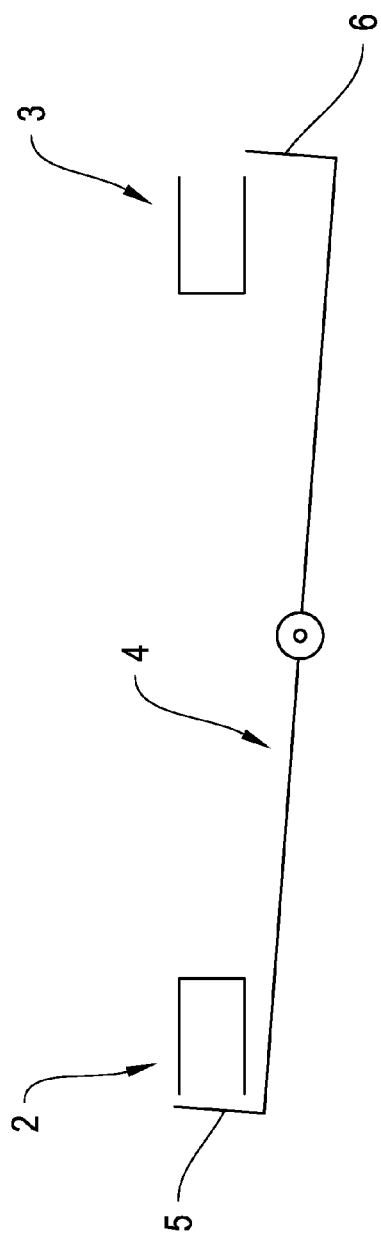
FIG. 6 presents a third embodiment of the invention with a stimulation plug available.
Figure 7:
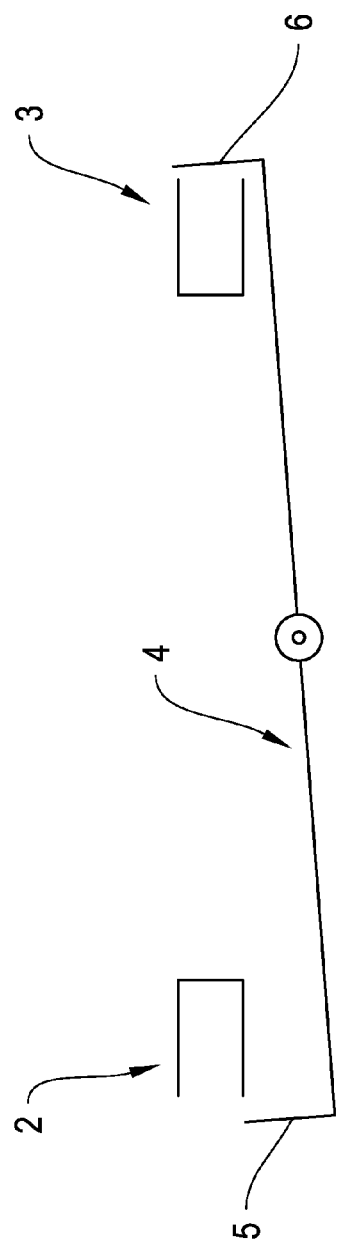
FIG. 7 presents the object of FIG. 6 with a charger plug available.
Figure 8:
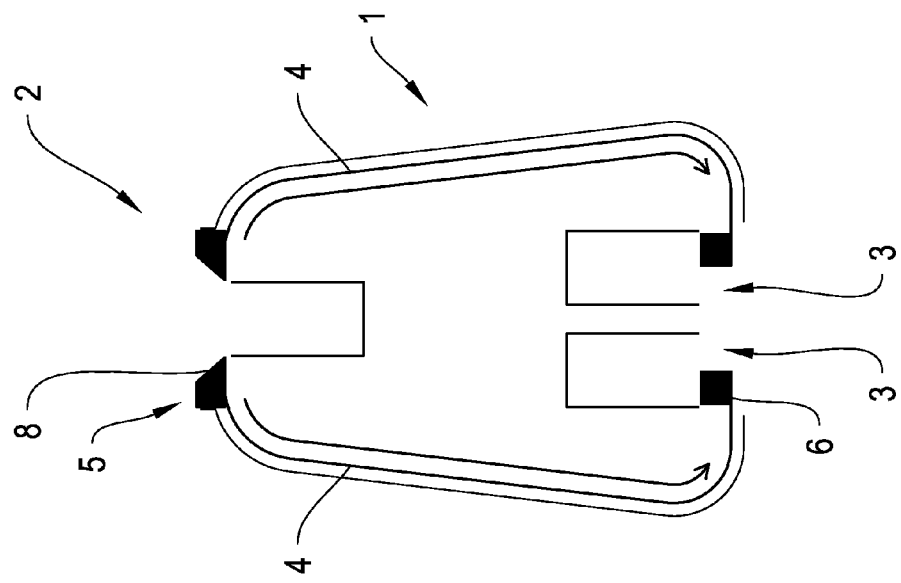
FIG. 8 presents a third embodiment of the invention with stimulation plugs available.
Figure 9:
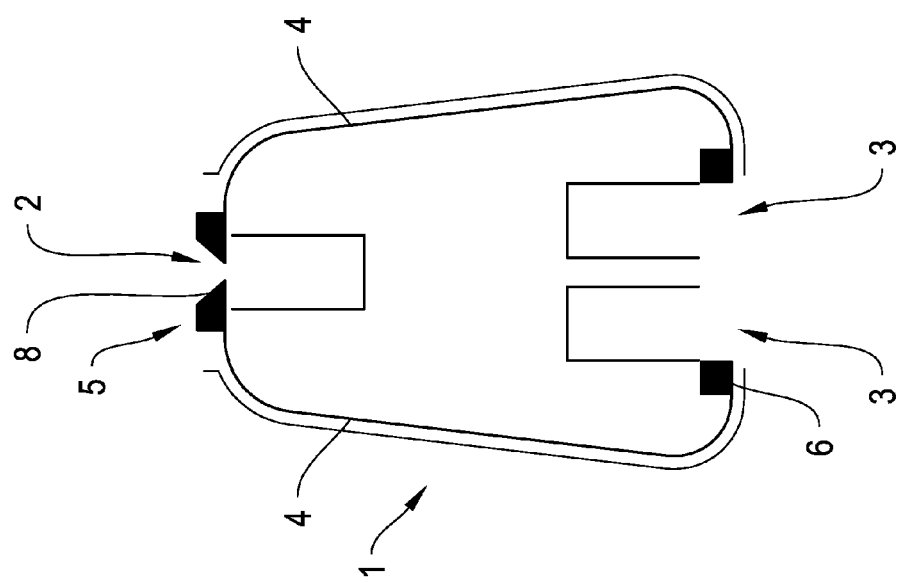
FIG. 9 presents the object of FIG. 8 with a charger plug available.

The embodiment of FIG. 6 also presents a locking rod 4 that pivots, but in a direction perpendicular to the main axis of the rod. In the embodiment of FIGS. 8 and 9, the charger plug 2 is located on a side of the housing 1 opposite to that where the stimulation plugs 3 are located. The mobile locking element 4 is formed by a semi-rigid tab, which is moved in response to the force exerted on the inclined surface 8 by the charger connector.

Figure 10:
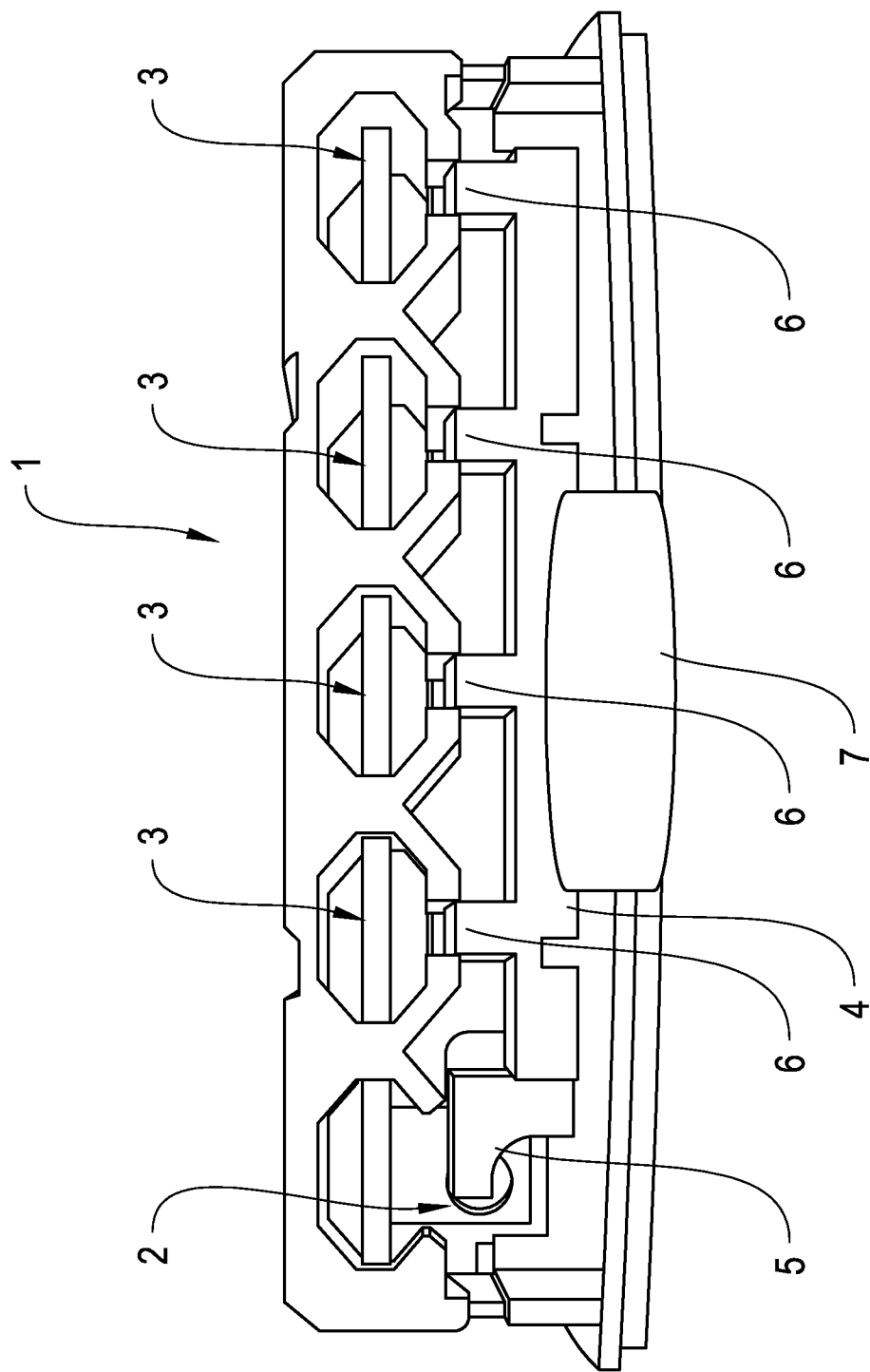
FIG. 10 presents a fourth embodiment of the invention with stimulation plugs available.
Figure 11:
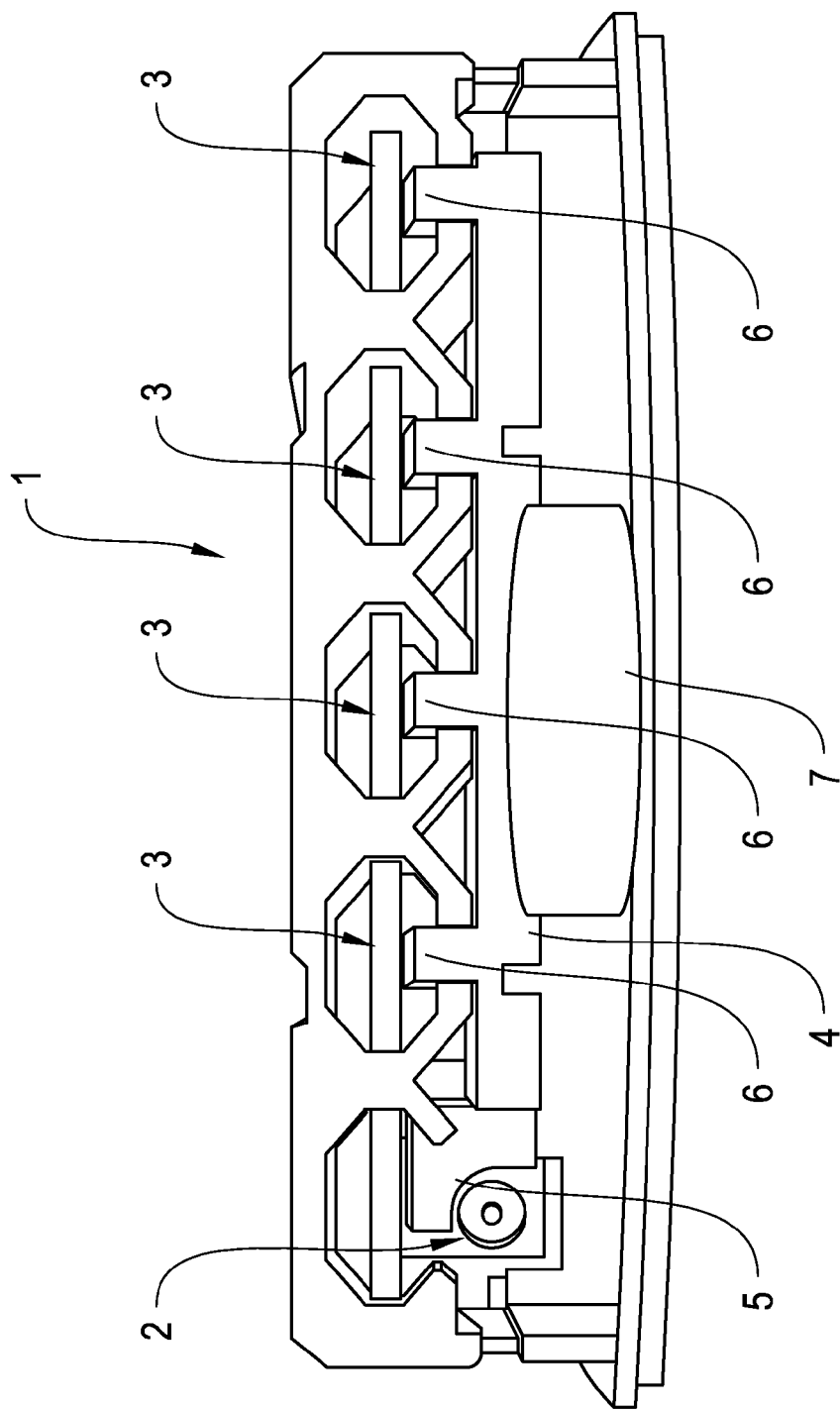
FIG. 11 presents the object of FIG. 10 with a charger plug available.

The embodiment of FIGS. 10 and 11 presents a mobile locking element 4 that is mobile in a vertical direction. In the configuration illustrated in FIG. 2, a spring (not shown) holds the mobile element 4 in a bottom position (rest position). The upward movement of the mobile element 4 is obtained manually through the intermediary of a thrust element 7 that the user must push upward.

The locking element 5 of the charger plug 2 is in the form of an inverted L. Four locking elements 6 for stimulation plugs 3 are located along the mobile locking element 4, perpendicular to the latter.

In the rest position (FIG. 10), the locking element of the charger plug 5 blocks the charger plug 2. The stimulation plugs 3 are available and can accommodate stimulation connectors.

If the user wants to insert the charger plug, he must first remove the stimulation connectors, push the thrust element 7 upward and insert the power supply connector.

Once this operation is completed (FIG. 11), the stimulation plugs are blocked by the corresponding locking elements 6.

According to the variant of the invention that is not shown, the thrust element 7 is eliminated. In this case, the locking element 5 of the charger plug 2 comprises an inclined surface of a form and function identical to that described previously.

Obviously, the invention is not limited to the above-mentioned examples.

The invention claimed is:

1. A housing for an electrostimulation system, the housing comprising:
    a first plug;
    a second plug; and
    a mobile locking member configured to partially cover the first plug but not the second plug in a rest position and to partially cover the second plug but not the first plug in an activated position, wherein insertion of a connector into the first plug transitions the mobile locking member from the rest position to the activated position, and removal of the connector from the first plug reverts the mobile locking member from the activated position to the rest position.

2. The housing of claim 1, wherein the mobile locking member is an elongate member.

3. The housing of claim 1, wherein the mobile locking member comprises a first protrusion that partially covers the first plug in the rest position, and a second protrusion that partially covers the second plug in the activated position.

4. The housing of claim 3, wherein the second protrusion is disposed along a length of the mobile locking member.

5. The housing of claim 4, wherein the second protrusion is configured to translate along a direction perpendicular to the length of the mobile locking member.

6. The housing of claim 4, wherein the second protrusion is configured to translate along a direction parallel to the length of the mobile locking member.

7. The housing of claim 3, wherein the first protrusion is disposed at an end of the mobile locking member.

8. The housing of claim 1, wherein the mobile locking member comprises one or more locking elements disposed on the mobile locking member that partially cover the first plug in the rest position and partially cover the second plug in the activated position.

9. The housing of claim 8, wherein the one or more locking elements include at least one of a tooth or a strip.

10. The housing of claim 1, wherein a connector inserted into the first plug exerts a force on an inclined surface of the mobile locking member and displaces the mobile locking member from the rest position to the activated position.

11. The housing of claim 10, wherein the mobile locking member is configured to be displaced in a direction substantially perpendicular to the direction of the exerted force.

12. The housing of claim 10, wherein the inclined surface of the mobile locking member is configured to receive a force exerted at an angle to the inclined surface by the connector inserted into the first plug.

13. The housing of claim 1, wherein the mobile locking member is moveable in a direction parallel to a plane passing through the first plug and the second plug.

14. The housing of claim 1, further comprising a spring that biases the mobile locking member in the rest position.

15. The housing of claim 14, wherein the spring exerts a force in a direction substantially perpendicular to a length of the mobile locking member.

16. The housing of claim 1, further comprising a pivot that affixes the mobile locking member to the housing, wherein the mobile locking member is configured to rotate from the rest position to the activated position along an axis of the mobile locking member that is collinear with the pivot and length of the mobile locking member.

17. The housing of claim 1, further comprising a pivot that affixes the mobile locking member to the housing, wherein the mobile locking member is configured to rotate from the rest position to the activated position along an axis perpendicular to the length of the mobile locking member.

18. The housing of claim 1, wherein the mobile locking member is moveable in a vertical direction from the rest position to the activated position.

19. The housing of claim 1, wherein the mobile locking member comprises a semi-rigid material, and is moveable along a curvilinear path from the rest position to the activated position.

\* \* \* \* \*

UNITED STATES PATENT AND TRADEMARK OFFICE
CERTIFICATE OF CORRECTION

PATENT NO. : 8,666,492 B2
APPLICATION NO. : 13/710842
DATED : March 4, 2014
INVENTOR(S) : Muller et al.

It is certified that error appears in the above-identified patent and that said Letters Patent is hereby corrected as shown below:

Title page (item 71, Applicant) at line 1, Change "Complex" to --Compex--.

Signed and Sealed this
Eighth Day of September, 2015

Michelle K. Lee
*Director of the United States Patent and Trademark Office*